United States Patent [19]
Shirai et al.

[11] Patent Number: 5,287,167
[45] Date of Patent: Feb. 15, 1994

[54] METHOD FOR MEASURING INTERSTITIAL OXYGEN CONCENTRATION

[75] Inventors: Hiroshi Shirai, Kanagawa; Mikio Watanabe, Sagae; Shinichiro Takasu, Tokyo, all of Japan

[73] Assignee: Toshiba Ceramics Co., Ltd., Tokyo, Japan

[21] Appl. No.: 738,043

[22] Filed: Jul. 31, 1991

[30] Foreign Application Priority Data

| Jul. 31, 1990 | [JP] | Japan | 2-203415 |
| Jul. 31, 1990 | [JP] | Japan | 2-203416 |
| Aug. 2, 1990 | [JP] | Japan | 2-205611 |
| Aug. 27, 1990 | [JP] | Japan | 2-224711 |
| Aug. 27, 1990 | [JP] | Japan | 2-224712 |
| Aug. 27, 1990 | [JP] | Japan | 2-224713 |
| Aug. 27, 1990 | [JP] | Japan | 2-224714 |
| Aug. 29, 1990 | [JP] | Japan | 2-227457 |

[51] Int. Cl.$^5$ .......................... G01J 4/00; G01N 21/00
[52] U.S. Cl. ...................... 356/364; 356/370; 356/351; 356/432; 356/433; 250/225
[58] Field of Search ............... 356/364, 365, 366, 367, 356/369, 368, 346, 345, 432, 433, 434, 435, 448, 436, 351; 250/360.1, 252.1, 341, 225

[56] References Cited

U.S. PATENT DOCUMENTS

| 3,623,818 | 11/1971 | Gardner | 356/448 |
| 4,290,698 | 9/1981 | Milana | 356/448 |
| 4,590,544 | 5/1986 | Edmonds et al. | 356/346 |
| 4,652,757 | 3/1987 | Carver | 250/360.1 |
| 5,007,741 | 4/1991 | Carver et al. | 356/369 |

OTHER PUBLICATIONS

K. Krishnan—"Precise and Rapid Measurement of Oxygen and Carbon etc." Proceedings of the Symposium on Defects in Silicon, 1983, pp. 285–291.
K. Graff—"Precise Evaluation of Oxygen Measurements on CZ-Silicon Wafers"—J. Electrochem, Soc: Jun. 1983 pp. 1378–1381.
F. Schomann et al—"Correction Factors for the Determination of Oxygen etc. " J. Electrochem, Soc. vol. 136, Jul. 1989 pp. 2025–2031.
J. A. A. Engelbrecht et al—"The Influence of Some Optical Parameters on IR Spectroscopy etc." Infrared Phys. vol. 26, No. 2, pp. 75–81.
J. A. A. Engelbrecht—"A Technique for Obtaining the Infrared Reflectivity of Back etc." J. Electrochem. Soc., vol. 137, No. 1, Jan. 1990, pp. 300–303.
Robert Graupner—"Analysis of Infrared Spectra for Oxygen Measurements etc." Silicon Processing, ASTM STP 804, 1983, pp. 459–468.
Leroueille—"Carbon Measurement in Thin Silicon Wafers etc." Applied Spectroscopy, vol. 36, No. 2, 1982, pp. 153–155.
"The Measurement of the Oxygen Concentration of Silicon Wafers by Fourier-transform-Infrared-Spectroscopy" Materialpreufung, vol. 32, p. 110 (1990).

*Primary Examiner*—Richard A. Rosenberger
*Assistant Examiner*—Hoa Q. Pham
*Attorney, Agent, or Firm*—Foley & Lardner

[57] ABSTRACT

The invention related to a method for determining a silicon wafer in which the interstitial oxygen concentration of a pulled silicon wafer is calculated on the basis of a light transmission characteristic measured by utilizing parallel polarized light incident at the brewster angle into the pulled silicon wafer and a further light transmission characteristic measured by utilizing parallel polarized light incident at the brewster angle into the floating zone silicon wafer function as a reference silicon wafer. The interstitial oxygen concentration value of the pulled silicon wafer is compared with a reference value to determine a defect in pulled silicon wafer.

23 Claims, 7 Drawing Sheets

METHOD FOR MEASURING INTERSTITIAL OXYGEN CONCENTRATION

BACKGROUND OF THE INVENTION

1. Field of the Invention

The present invention relates to a method for making a silicon wafer. In particular, the present invention relates to a method for making a silicon wafer in which the interstitial oxygen concentration of a pulled silicon wafer is calculated on the basis of a light transmission characteristic measured by utilizing parallel polarized light indicated at the Brewster angle into the pulled silicon wafer and a further light transmission characteristic measured by utilizing parallel polarized light incident at the Brewster angle into a floating zone silicon wafer functioning as a reference silicon wafer. The calculated value is then compared with a reference value so as to exclude any pulled silicon wafer having defective interstitial oxygen concentration.

2. Description of Related Art

In the conventional method for making silicon wafers, a pulled silicon wafer is picked up from a production line in order to inspect it. A floating zone type silicon wafer is utilized as a reference wafer since the oxygen concentration of such wafers is known to be negligibly small. The reference silicon wafer is prepared so as to have substantially the same optical behavior as that of the pulled silicon wafer, for example, by mirror polishing and chemically polishing of the front and rear faces thereof, depending on the condition of the pulled silicon wafer when it is picked up. After that, an infrared ray impinges on both the pulled silicon wafer and the reference silicon wafer at the same time to thereby measure a light transmission characteristic of the pulled silicon wafer and the floating zone silicon wafer so that the interstitial oxygen concentration of the pulled silicon wafer is calculated. According to such calculated interstitial oxygen concentration values, it is determined whether or not the pulled silicon wafer is defective.

Such a conventional silicon wafer production method has the following disadvantages because in the conventional method the pulled silicon wafer and the floating zone silicon wafer must have substantially the same optical behavior, e.g., they must both be mirror polished.

(i) A lot of time and complicated measuring operations are required. In particular, the reference silicon wafer must be treated so as to correspond to the picked-up silicon wafer or visa versa.

(ii) It is not possible in practice to inspect all of pulled silicon wafers on a production line.

(iii) Since machining takes place prior to the measurement, detective wafers are unnecessarily machined, thereby reducing efficiency.

(iv) As a result, it is difficult to improve the production efficiency of the production line.

SUMMARY OF THE INVENTION

It is an object of the present invention to provide a method for making a silicon wafer in which a floating zone silicon wafer having both front and rear faces mirror polished can be used as a reference silicon wafer without any additional treatment.

It is another object of the present invention to provide a silicon wafer measuring method in which the measuring operation is simple.

It is a further object of the present invention to provide a method for measuring interstitial oxygen concentration of a silicon wafer in which all of pulled silicon wafers on a production line can be detected.

According to the present invention, a silicon wafer measuring method includes:

(a) a first step of measuring a light transmission characteristic ($I_{OBS}$) of the pulled silicon wafer by utilizing parallel polarized light incident at the Brewster angle on the pulled silicon wafer, (b) a second step of measuring a light transmission characteristic ($I_O$) of a floating zone silicon wafer functioning as a reference silicon wafer both front and rear faces of which are mirror polished, by utilizing parallel polarized light incident at the Brewster angle on the floating zone silicon wafer, and (c) a third step of calculating an interstitial oxygen concentration [Oic] on the basis of the light transmission characteristic ($I_{OBS}$) of the pulled silicon wafer measured during the first step and the light transmission characteristic ($I_O$) of the floating zone silicon wafer measured during the second step.

According to the present invention, also, a silicon wafer production method in which a pulled silicon wafer cut from a pulled silicon single crystal is subject to a series of treatments, includes:

(a) a first step of measuring a light transmission characteristic ($I_{OBS}$) of the pulled silicon wafer by utilizing parallel polarized light incident at the Brewster angle into the pulled silicon wafer, (b) a second step of measuring a light transmission characteristic ($I_O$) of a floating zone silicon wafer functioning as a reference silicon wafer both front and rear faces of which are mirror polished, by utilizing parallel polarized light incident at the Brewster angle into the floating zone silicon wafer, and (c) a third step of calculating an interstitial oxygen concentration [Oic] on the basis of the light transmission characteristic ($I_{OBS}$) of the pulled silicon wafer measured during the first step and the light transmission characteristic ($I_O$) of the floating zone silicon wafer measured during the second step.

The series of treatments to which the pulled silicon wager is subject to include: mechanical cutting, mechanical polishing, chemically polishing, mirror polishing, inspecting, removing, washing, and gettering.

It is preferable that the method of the present invention includes further:

(d) a fourth step of comparing the interstitial oxygen concentration [Oic] of the pulled silicon wafer measured during the third step with a reference value, and (e) a fifth step of removing the single-side polished silicon wafer if its interstitial oxygen concentration [Oic] is one of above or below the reference value so as to determine a defective wafer in view of the results compared during the fourth step.

During the first step, the light transmission characteristic of the pulled silicon wafer can be measured in various ways. One example is a pulled silicon wafer which has a mirror polished front surface and non-polished rear surface. In another example, both front and rear surfaces are chemically polished but not mirror polished. In a further example, both front and rear surfaces are mechanically polished but not chemically polished. Another example is when the wafer is cut from a pulled silicon single crystal and then washed but not polished in any manner.

The term "parallel polarized light" means polarized light which is substantially linearly polarized in a direction parallel to the incident plane (the plane defined by the direction of the incident light and the normal to the wafer surface). The wafer surface may be, for example, a non-polished pulled silicon wafer, a mechanically, chemically and/or mirror polished pulled silicon wafer and a mirror polished floating zone silicon wafer. Also, the term "pulled silicon wafer" means a silicon wafer which is sliced or cut from a pulled silicon single crystal produced by a pulling method or so called Czochralski method and then treated, if desired, in various manners. Such a silicon wafer is usually made by a series of steps of cutting (slicing), mechanical polishing (lapping), chemical polishing (etching), and mirror polishing (which is a combination of mechanical/chemical fine polishing) in order together with intermediate washing and optional gettering steps although the present invention is not limited to such precise steps. The chemical polishing step is performed after the mechanical polishing step. The mechanical polishing step is used to remove damaged or broken layers in the front and rear surfaces of the silicon wafer which are formed during the step of cutting a single crystal. In addition, the term "floating zone silicon wafer" means a silicon wafer which is cut from a silicon single crystal made by the well-known floating zone melting method.

The present invention can have the following advantageous effects:

(i) A floating zone silicon wafer both front and rear surfaces of which are mirror polished can be used as it is without any additional treatment;

(ii) The operation of measuring interstitial oxygen concentration [Oic] of a pulled silicon wafer can be simple;

(iii) The step of measuring interstitial oxygen concentration [Oic] of a pulled silicon wafer can be carried out at a desired position in a production line in order to detect all wafers; and (iv) The production coefficient on the production line can be improved.

BRIEF DESCRIPTION OF THE DRAWINGS

The invention is described in reference to the following detailed description taken in conjunction with the drawings in which.

DETAILED DESCRIPTION OF THE PREFERRED EMBODIMENTS

Embodiment 1

Figure 1:
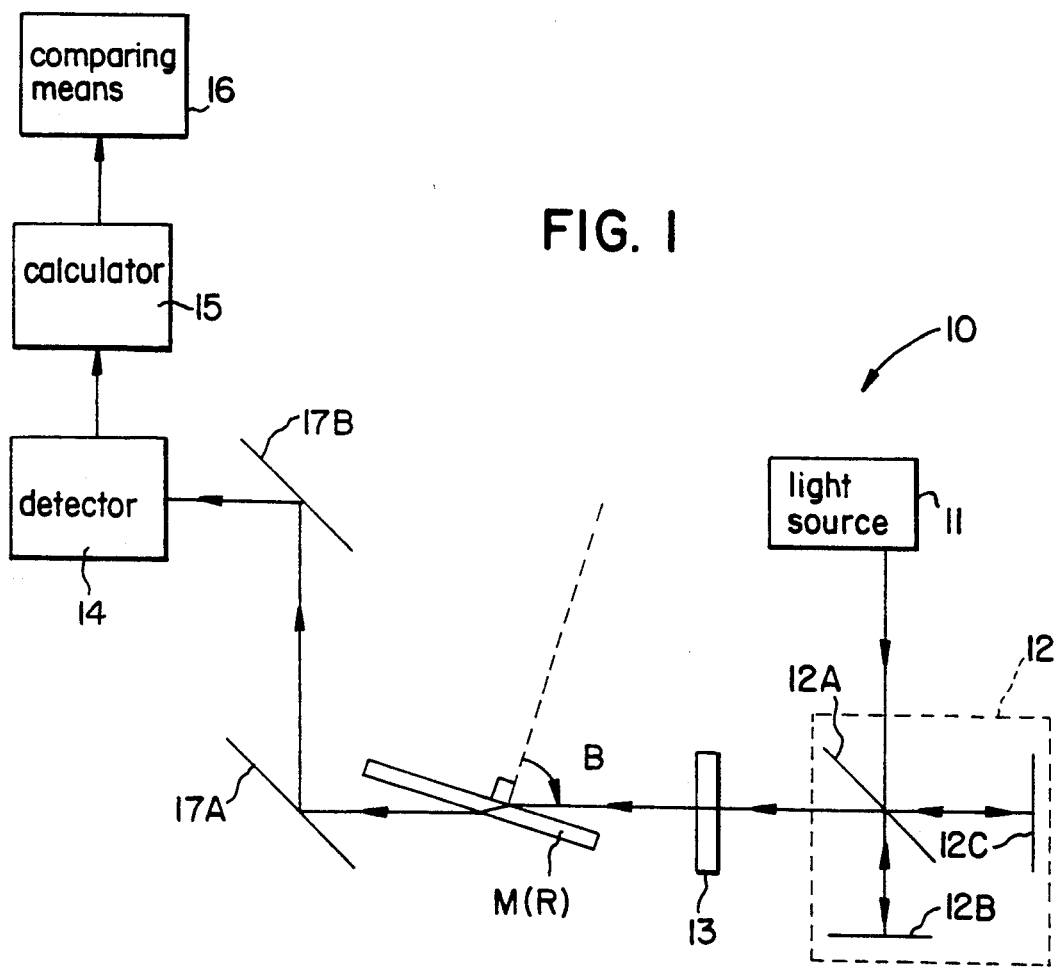
FIG. 1 is a schematic view showing an apparatus for carrying out a preferred silicon wafer production method according to an embodiment of the present invention.

A first embodiment of the present invention will be described.

According to the first embodiment of the present invention, a method for making a silicon wafer includes the step of measuring interstitial oxygen concentration prior to the steps of gettering and mirror polishing after the washing step accompanied by the chemically polishing step for silicon wafers on a production line.

The measuring step in the silicon wafer production method according to the present invention includes a first step of measuring a light transmission characteristic (herein called transmitted light intensity $I_{OBS}$) of a pulled silicon wafer by using parallel polarized light incident at the Brewster angle B into the pulled silicon wafer. Both the front and rear faces of the wafer are previously chemical polished during a chemical polishing step within the production line and then washed during a washing step. A second step of the method involves measuring a light transmission characteristic (herein called transmitted light intensity $I_O$) of a floating zone silicon wafer functioning as a reference silicon wafer, having mirror polished front and rear faces by directing parallel polarized light incident at the Brewster angle B into the reference or floating zone silicon wafer. A third step involves calculating an interstitial oxygen concentration [Oic] on the basis of the light transmission characteristic or transmitted light intensity $I_{OBS}$ of the chemically polished pulled silicon wafer measured during the first step and the light transmission characteristic or transmitted light intensity $I_O$ of the mirror polished floating zone silicon wafer or reference silicon wafer measured during the second step. A fourth step involves comparing the interstitial oxygen concentration [Oic] of the pulled silicon wafer calculated during the third step with a reference value, and a fifth step involves removing a pulled silicon wafer if its interstitial oxygen concentration [Oic] is outside of a range about the reference value so as to be defective in view of the comparison results in the fourth step.

During the first and second steps, the parallel polarized light enters into both the chemically polished pulled silicon wafer and the mirror polished floating zone silicon wafer at Brewster angle B. This is because any substantial reflection is avoided at the Brewster angle when the parallel polarized light moves in and through the chemically polished pulled silicon wafer and the mirror polished floating zone silicon wafer whereby multiple reflections can be avoided within the chemically polished pulled silicon wafer and the mirror polished floating zone silicon wafer.

During the second step, the floating zone silicon wafer is used as a reference silicon wafer because the interstitial oxygen concentration $[Oi_F]$ of the floating zone silicon wafer is much smaller than that of the pulled silicon wafer.

Also, both front and rear surfaces of the floating zone silicon wafer are mirror polished because the incidence light or parallel polarized light is intended to be prevented from being scattered at both front and rear surfaces thereof.

During the third step, the interstitial oxygen concentration of the pulled silicon wafer is calculated on the basis of the light transmission characteristic or transmitted light intensity $I_{OBS}$ of the chemically polished pulled silicon wafer measured during the first step and the light transmission characteristic or transmitted light intensity $I_O$ of the floating zone silicon wafer measured during the second step. This calculation step is explained below.

First, by using the light absorption coefficient E resulting from the vibration of the interstitial oxygen in the pulled silicon wafer and the conversion coefficient k which may be taken to be $3.03 \times 10^{17}$ number/cm$^2$, the interstitial oxygen concentration [Oic] of the pulled silicon wafer can be expressed by the following formula:

$$[Oic] = k \times E$$

By using the light absorbance A of the silicon wafer having a thickness d with the wave number of 1106 cm$^{-1}$ resulting from the vibration of the interstitial oxygen and the optical path (L=1.042d) of the parallel polarized light which enters at Brewster angle B, the light absorption coefficient E of the pulled silicon wafer can be expressed according to Lambert-Beer's law as follows:

$$E = A/L = A/1.042d$$

By using the light transmission characteristic or transmitted light intensity (in the general case designated I) of the pulled silicon wafer of which both front and rear surfaces are chemically polished, and the light transmission characteristic or transmitted light intensity $I_O$ of the floating zone silicon wafer which is mirror polished, the light absorbance A of the pulled silicon wafer can be expressed as follows:

$$A = \operatorname{Ln}(I/I_0)^{-1}$$

Thus, by using the light transmission characteristic or transmitted light intensity $I_{OBS}$ of the chemically polished pulled silicon wafer, the light transmission characteristic or transmitted light intensity $I_O$ of the mirror polished floating zone silicon wafer, the light scattering characteristic or scattered light intensity $I_{S1}$ of the chemically polished pulled silicon wafer at its front surface, and the light scattering characteristic or scattered light intensity $I_{S2}$ of the chemically polished pulled silicon wafer at its rear surface, the light absorbance A can be also expressed as follows:

$$A = \operatorname{Ln}[(I_{OBS} + I_{S1} + I_{S2})/I_0]^{-1}$$

Accordingly, the interstitial oxygen concentration [Oic] of the pulled silicon wafer can be calculated as follows:

$$[Oic] = (k/1.042d) \times \operatorname{Ln}[(I_{OBS} + I_{S1} + I_{S2})/I_0]^{-1}$$

The value of $\operatorname{Ln}[(I_{OBS} + I_{S1} + I_{S2})/I_0]^{-1}$ can be obtained from the light absorbance characteristic which is an inverse of the natural logarithm of the ratio of the total of the light transmission characteristic or transmitted light intensity ($I_{OBS}$) of the chemically polished pulled silicon wafer, the light scattering characteristic or scattered light intensity ($I_{S1}$) at the front surface of the chemically polished pulled silicon wafer and the light scattering characteristic or scattered light intensity ($I_{S2}$) at the rear surface of the chemically polished pulled silicon wafer to the light transmission characteristic or transmitted light intensity ($I_o$) of the mirror polished floating zone silicon wafer.

Figure 3:
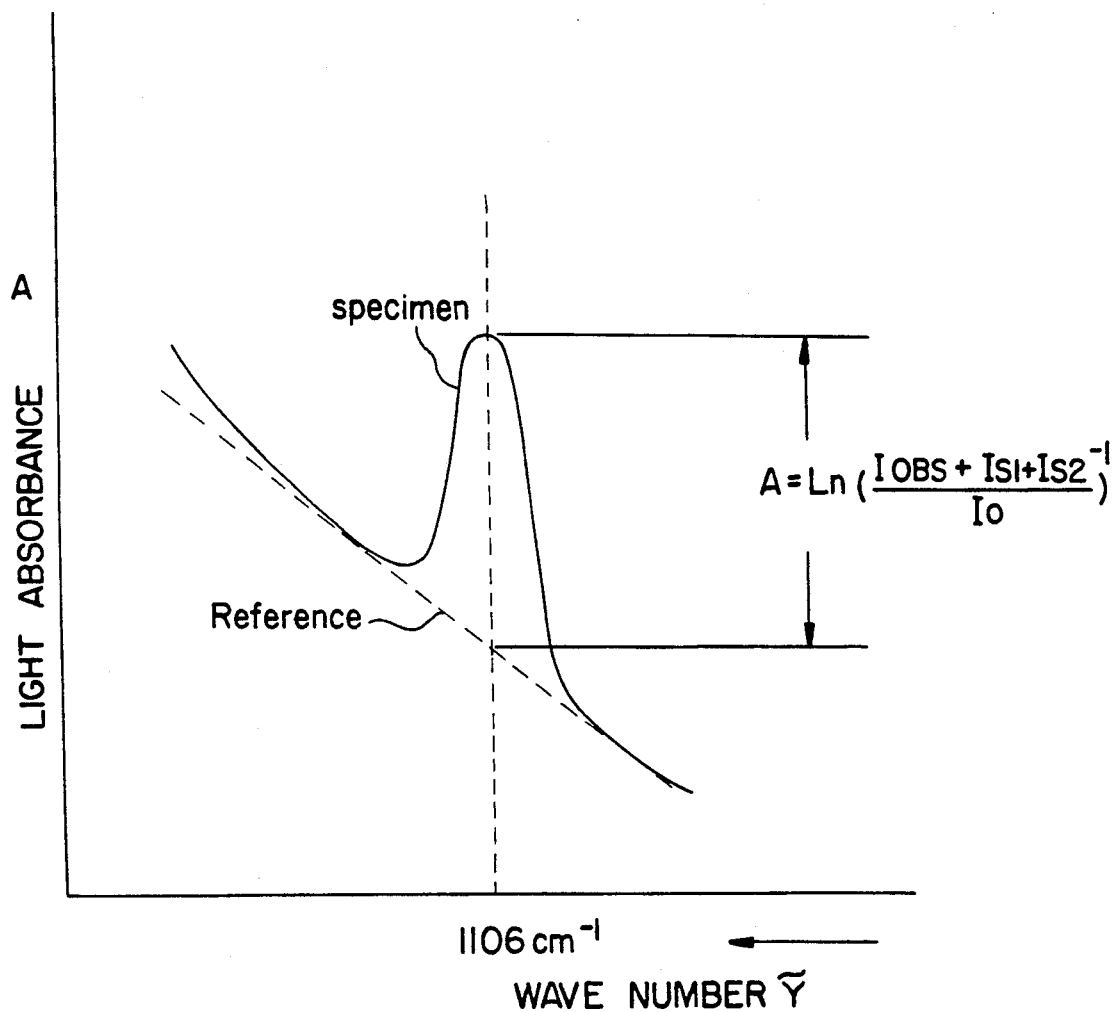
FIG. 3 is a graph explaining the measurement principle in accordance with the present invention.

For example, the value of $\operatorname{Ln}[(I_{OBS} + I_{S1} + I_{S2})/I_0]^{-1}$ can be obtained as shown in FIG. 3, by using the difference between the peak value of the light absorption characteristic designated by the solid line (characteristic of the Si-O absorption line of wave number 1106 cm$^{-1}$) when the interstitial oxygen concentration [Oic] is not zero, i.e., the pulled silicon wafer, and the value of the light absorption characteristic designated by the inclined dotted line when the interstitial oxygen concentration [Oic] is zero, i.e., the floating zone silicon wafer.

An apparatus for carrying out the first embodiment of the present invention is explained below.

Figure 2:
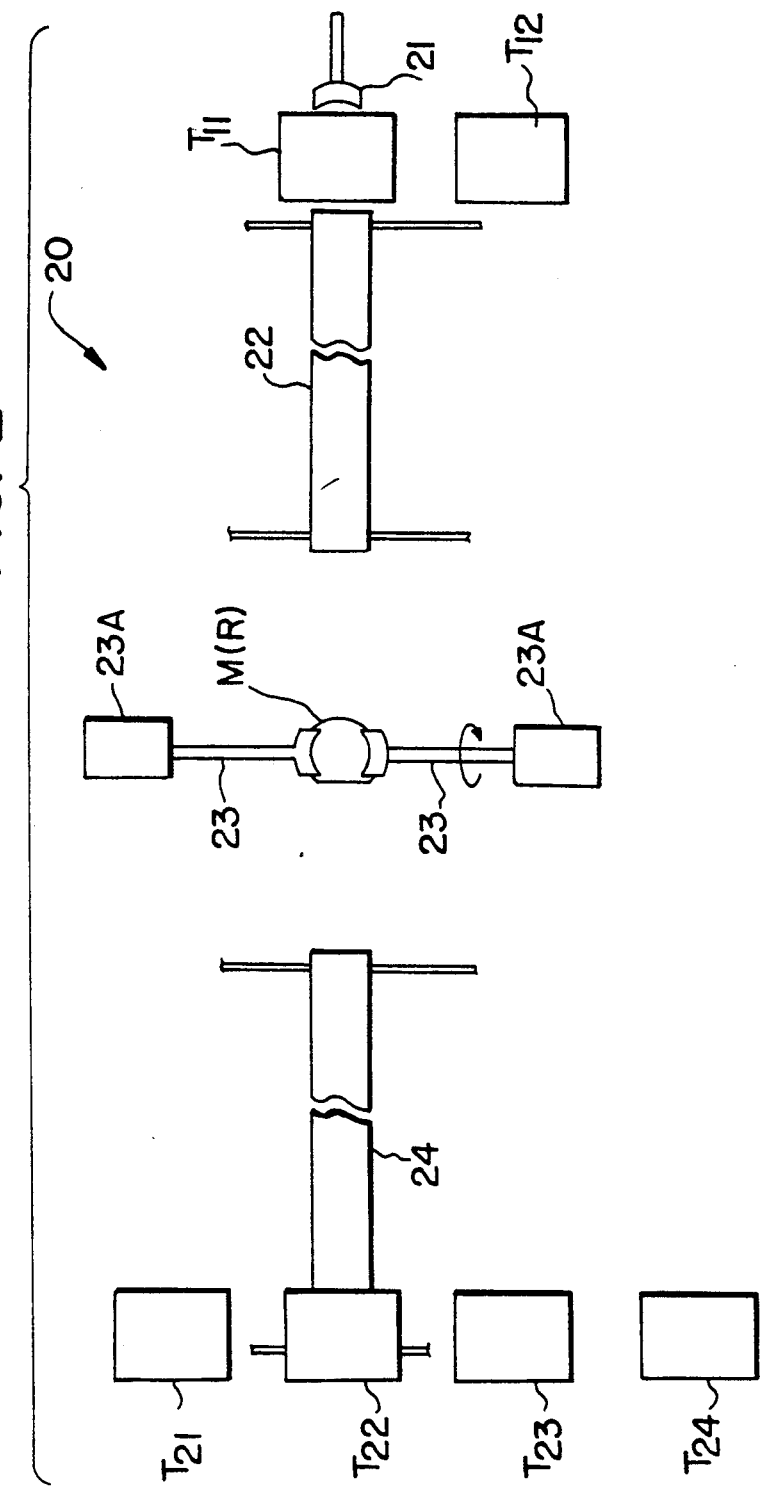
FIG. 2 is a schematic view showing a transfer means for use in the embodiment of the present invention.

Referring to FIGS. 1 and 2, a measuring apparatus 10 for carrying out the first embodiment includes a light source 11 such as a globe lamp and a Michelson interferometer 12 for forming interference light beams. The interferometer 12 uses a semi-transparent mirror 12A, a movable mirror 12B and a fixed mirror 12C. The apparatus further comprises a polarizer 13 for providing a specimen or chemically polished pulled silicon wafer M and a reference silicon wafer or mirror polished floating zone silicon wafer R with parallel polarized light which is polarized from the interference light given by the Michelson interferometer 12. The specimen M is transferred into the measurement position by a transfer means 20 shown in Figs. The apparatus further includes, a detector 14 for detecting the light transmission characteristic (or transmitted light intensity $I_{OBS}$ of the parallel polarized light) of the specimen M and the light transmission characteristic (or transmitted light intensity $I_O$ of the parallel polarized light) of the reference R, a calculator 15 connected to the detector 14 for calculating the interstitial oxygen concentration of the specimen M after the light absorbance characteristic is calculated on the basis of the light transmission characteristic or transmitted light intensity $I_{OBS}$ of the specimen M and the light transmission characteristic or transmitted light intensity $I_O$ of the reference R, and a means for comparing a reference value such as an upper limit reference value and a lower limit reference value with a value of the interstitial oxygen concentration which is calculated by the calculator 15.

If desired, reflecting mirrors 17A, 17B are provided between the specimen M and the detector 14 and/or between the reference R and the detector 14. Also, a reflecting mirror (not shown) can be arranged between the Michelson interferometer 12 and the polarizer 13.

The transfer means 20 includes a pushing member 21 for pushing the specimen M and the reference R from a plurality of transfer containers $T_{11}$, $T_{12}$ one by one, a transfer belt 22 for transferring the specimen M and the reference R pushed by the pushing means 21 one by one from one end thereof to the other end thereof, a holding means 23 for holding the specimen M and the reference R one by one at the other end of the transfer belt 22 and then transferring the same to a measuring area where the specimen M and the reference R are rotated by a rotation means 23A until they are oriented at the Brewster angle B with respect to the parallel polarized light. After the interstitial oxygen concentration thereof is measured, the specimen M and the reference R are again rotated by the rotation means 23A so as to come back to their original position and then move out of the measuring area. The transfer means 20 further includes another transfer belt 24 for receiving the specimen M and the reference R which are released from the measuring area by means of the holding means 23 and then transferring them from one end of the transfer belt 24 to the other end thereof where a plurality of transfer containers $T_{21}$, $T_{22}$, $T_{23}$, $T_{24}$ are placed.

Although in the illustrated embodiment the reference R is contained in the transfer container $T_{12}$, the reference R and the specimen M together can be contained in the transfer container $T_{11}$. In this case, the transfer container $T_{12}$ can be omitted.

For example, the transfer containers $T_{21}$, $T_{22}$, $T_{23}$, $T_{24}$ are used, respectively, for containing defective specimen M which has a value of interstitial oxygen concentration more than the upper limit reference value, a transfer container for containing proper specimen M which has a value of interstitial oxygen concentration between the upper limit reference value and the lower limit reference value, a transfer container for containing defective specimen M which has a value of interstitial oxygen concentration less than the lower limit reference value, and a transfer container for containing the reference R. These transfer containers $T_{21}$, $T_{22}$, $T_{23}$ are designed to receive the specimens M in response to the comparison results of the comparison means 16 in the measuring apparatus 10. These transfer containers move to an end of the transfer belt 24 so as to receive the reference R.

In the measuring apparatus 10, the Michelson interferometer 12 receives the light from the light source and then produces interference light. This interference light is further filtered so as to obtain parallel polarized light by means of the polarizer 13. After that, the parallel polarized light is incident at the Brewster angle B into the specimen M and the reference R which are transferred to the measuring area by the transfer means 20.

The light is absorbed and scattered in the specimen M and the reference R according to the optical properties thereof. Therefore, the light absorbance characteristic, which can be calculated by the calculator 15 on the basis of the signals detected by the detector 14, is shown in FIG. 3 by way of example.

According to FIG. 3 or a table corresponding thereto, the calculator 15 calculates the following formula:

$$Ln[(I_{OBS}+I_{S1}+I_{S2})/I_0]^{-1}$$

After that, the calculator 15 calculates the light absorbance coefficient E of the chemically polished, pulled silicon wafer by the following formula:

$$E=(1/1.042d)\times Ln[(I_{OBS}+I_{S1}+I_{S2})/I_0]^{-1}$$

In addition, the calculator calculates the interstitial oxygen concentration [Oic] of the specimen M of the chemically polished pulled silicon wafer M by the following formula:

$$[Oic]=(k/1.042d)\times Ln[(I_{OBS}+I_{S1}+I_{S2})/I_0]^{-1}$$

After that, the comparison means 16 compares the reference value (for example, the upper limit reference value and for the lower limit reference value) with the value of the interstitial oxygen concentration [Oic] of the specimen or chemically polished, pulled silicon wafer M which is calculated by the calculator 15.

The results of the comparison means 16 are sent to means for controlling the transfer means 20 to be used in transferring the specimen M and the reference R into the transfer containers $T_{21}$, $T_{22}$, $T_{23}$, $T_{24}$.

EXAMPLES 1 TO 22

Working examples of the first embodiment will be explained so that a method for making a silicon wafer according to the present invention will be fully understood.

As shown in Table 1, interstitial oxygen concentration [Oic] of plural pulled silicon wafers were measured according to the present invention. First, after both front and rear faces of the silicon wafers were chemically polished, interstitial oxygen concentration [Oic] thereof were measured.

After that, both front and rear surfaces of the chemically polished pulled silicon wafers were mirror polished. In such a mirror polished condition, the interstitial oxygen concentration [Oic]* of each pulled silicon wafer was measured according to the present invention.

Figure 4:
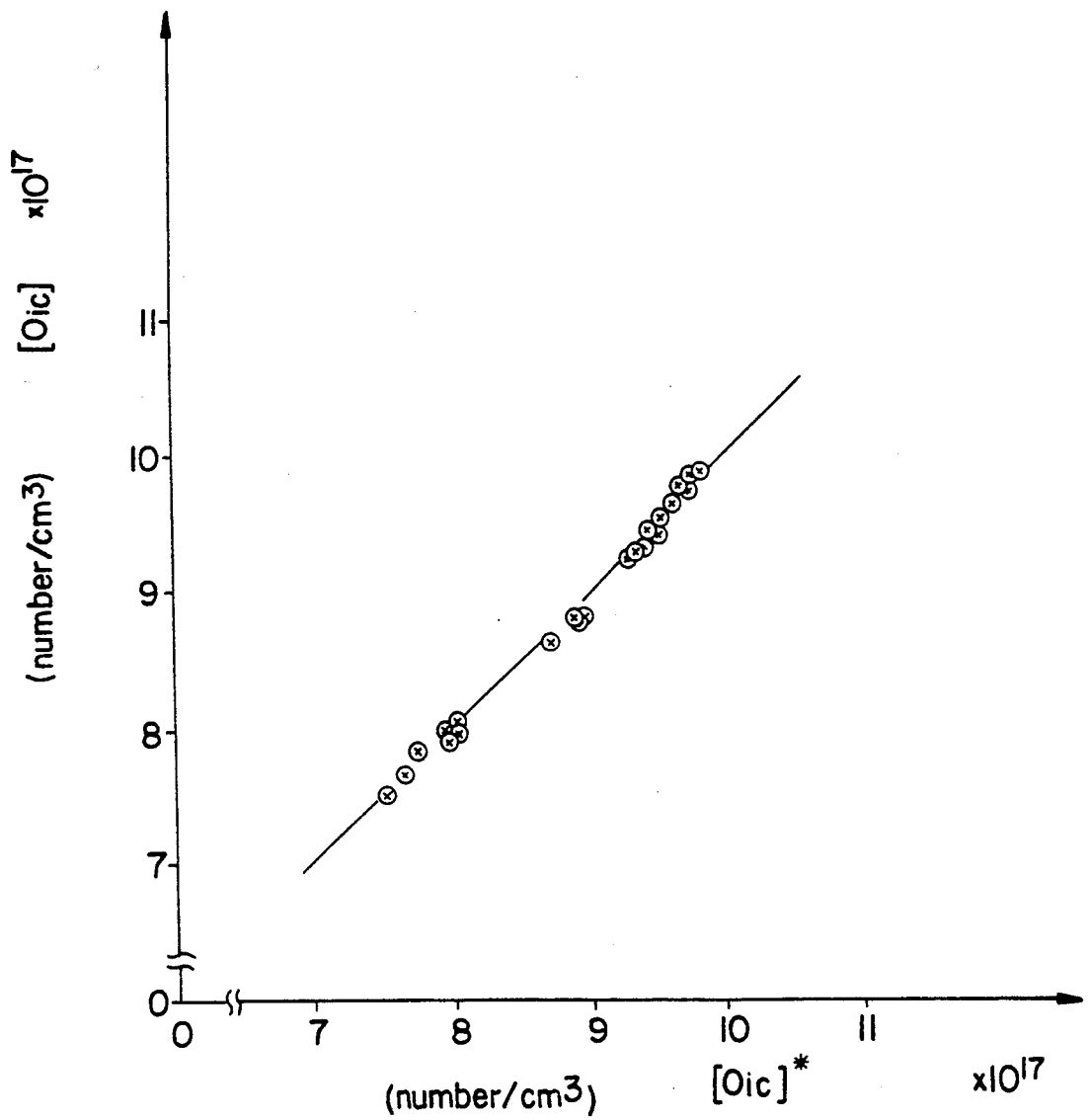
FIG. 4 is a graph showing the results of working examples in accordance with another embodiment of the present invention.

Such measured results of the interstitial oxygen concentration [Oic] of the chemically polished pulled silicon wafers and the interstitial oxygen concentration [Oic]* of the subsequently produced mirror polished pulled silicon wafers are plotted along the Y-axis and X-axis, respectively, in FIG. 4. This graph shows that the former reasonably corresponds to the latter so that the test results are positioned along the line X=Y.

It is apparent from the examples 1 to 22 that, according to the present invention, the chemically polished pulled silicon wafers and the mirror polished floating zone silicon wafers can be used as specimen and references, respectively, in order to directly measure interstitial oxygen concentration [Oic] of the pulled silicon wafers on the production line. Thus, it is not necessary to make the measurement of the oxygen concentration [Oic] on the mirror polished pulled silicon wafer.

TABLE 1

| Example No. | interstitial oxygen concentration [Oic] of chemically polished pulled silicon wafer ($\times 10^{17}$ number/cm$^3$) | interstitial oxygen concentration [Oic]* of mirror polished pulled silicon wafer ($\times 10^{17}$ number/cm$^3$) |
|---|---|---|
| 1 | 7.51 | 7.55 |
| 2 | 7.87 | 7.77 |
| 3 | 7.66 | 7.68 |
| 4 | 7.98 | 7.99 |
| 5 | 7.93 | 8.00 |
| 6 | 9.41 | 9.46 |
| 7 | 9.54 | 9.55 |
| 8 | 9.73 | 9.76 |
| 9 | 9.85 | 9.79 |
| 10 | 9.44 | 9.54 |
| 11 | 9.32 | 9.37 |
| 12 | 9.36 | 9.42 |
| 13 | 9.27 | 9.35 |
| 14 | 7.99 | 8.02 |
| 15 | 8.02 | 8.05 |
| 16 | 8.64 | 8.70 |
| 17 | 8.80 | 8.91 |
| 18 | 9.79 | 9.70 |
| 19 | 9.88 | 9.85 |
| 20 | 9.65 | 9.64 |
| 21 | 8.83 | 8.98 |
| 22 | 8.83 | 8.84 |

Although the above-stated embodiment utilizes a Michelson interferometer 12, the present invention is not restricted to such an embodiment. For example, a spectrometer can be used in place of the Michelson interferometer.

In general, the production of the pulled silicon wafer involves growing the silicon crystal, cutting the crystal, washing and lapping the surface to provide a coarse polishing (mechanically polishing), washing and chemically polishing the surface and then washing and mirror polishing the surface. A gettering step may be used at various points in the process such as before and/or after the mirror polishing step.

Although in the above-stated embodiment the interstitial oxygen concentration [Oic] is measured prior to the gettering step following the chemically polishing step, the present invention is not restricted to such an embodiment. For example, the interstitial oxygen concentration [Oic] can be measured at any position or place after the chemically polishing step and prior to the mirror polishing step. For instance, the interstitial oxygen concentration [Oic] can be measured during other types of measurements which may be made on the silicon wafer.

Embodiment 2

A second embodiment of the present invention will be explained with respect to the construction and operation thereof.

The second embodiment of the present invention has substantially the same construction as that of the first embodiment except that, in addition to the interstitial oxygen concentration measuring step prior to the gettering step, the interstitial oxygen concentration measuring step is carried out after the gettering step.

The interstitial oxygen concentration measuring step after the gettering step has the same construction as that of the interstitial oxygen concentration measuring step prior to the gettering step which corresponds to the measuring step in the first embodiment.

The operation of the second embodiment can be easily understood by taking into consideration that of the first embodiment. Thus, the explanation thereof is omitted.

Embodiment 3

A third embodiment of the present invention will be explained with respect to the construction and operation thereof.

The third embodiment of the present invention has substantially the same construction as that of the first embodiment except that, in place of the interstitial oxygen concentration measuring step prior to the gettering step, the interstitial oxygen concentration measuring step is carried out after the gettering step.

The interstitial oxygen concentration measuring step after the gettering step has the same construction as that of the measuring step in the first embodiment.

The operation of the third embodiment can be easily understood by taking into consideration that of the first embodiment. Thus, the explanation thereof is omitted.

Embodiment 4

Embodiment 4 of the present invention has substantially the same construction as that of embodiment 1 except that the fourth comparing step and the fifth removing step of embodiment 1 are omitted.

The operation of embodiment 4 can be easily understood by taking into consideration that of embodiment 1.

Embodiment 5

A fifth embodiment of the present invention is similar to the first embodiment. In the fifth embodiment, however, the specimen has a mirror polished front face and non-polished rear face, and the light path L is 1.041d in place of 1.042d. In order to easily ascertain front and rear faces of the silicon wafer during subsequent treatments thereof, only the front face is mirror polished while the rear face is not polished. Therefore, in FIG. 3, the light absorbance A is expressed as follows:

$$A = \text{Ln} \,[(I_{OBS}+I_S)/I_O]^{-1}$$

where Is = the scattered light intensity of the one-side mirror polished pulled wafer at the rear surface.

The measuring step includes a first step of measuring a light transmission characteristic or transmitted light intensity $I_{OBS}$ of a pulled silicon wafer (herein called one-face polished silicon wafer) by directing parallel polarized light at the Brewster angle B into the pulled silicon wafer. Only a front face of the wafer is mirror polished during the mirror polishing step within the production line and then washed during a washing step. A second step consists of measuring a light transmission characteristic or transmitted light intensity $I_O$ of a floating zone silicon wafer functioning as a reference silicon wafer by using parallel polarized light at the Brewster angle B directed into the reference silicon wafer or floating zone silicon wafer. Both the front and rear faces of the reference wafer are mirror polished. A third step consists of calculating an interstitial oxygen concentration [Oic] on the basis of the light transmission characteristic or transmitted light intensity $I_O$ of the one-face polished pulled silicon wafer measured during the first step and the light transmission characteristic or transmitted light intensity $I_O$ of the mirror polished floating zone silicon wafer or reference silicon wafer measured during the second step. A fourth step consist of comparing the interstitial oxygen concentration [Oic] of the pulled silicon wafer measured during the third step with a reference value (for example, an upper limit reference value and/or lower limit reference value), and a fifth step of removing a defective pulled silicon wafer if its interstitial oxygen concentration [Oic] is not within the reference value (for example, between the upper limit reference value and the lower limit reference value).

During the first and second steps, the parallel polarized light enters into both the one-face polished pulled silicon wafer and the mirror polished floating zone silicon wafer at the Brewster angle B because any substantial reflection is avoided when the parallel polarized light moves in and through the one-face polished pulled silicon wafer and the mirror polished floating zone silicon wafer whereby multiple reflections can be avoided within the one-face polished pulled silicon wafer and the mirror polished floating zone silicon wafer.

During the third step, the interstitial oxygen concentration of the one-face polished pulled silicon wafer is calculated on the basis of the light transmission characteristic or transmitted light intensity $I_{OBS}$ of the mirror polished pulled silicon wafer measured during the first step and the light transmission characteristic or transmitted light intensity $I_O$ of the floating zone silicon wafer measured during the second step. This calculation is substantially the same as that of the first embodiment.

Examples 23 to 40

Working examples of the fifth embodiment will be explained so that a method for making a silicon wafer according to the present invention will be fully understood.

As shown in Table 2, interstitial oxygen concentration [Oic] of plural pulled silicon wafers were measured according to the present invention. First, a silicon wafer, only a front surface of which was mirror polished, that is, a one-face polished silicon wafer was measured with respect to its interstitial oxygen concentration [Oic].

After that, the pulled silicon wafer was mirror polished on the rear surface thereof to produce a two-face polished specimen, and the interstitial oxygen concentration [Oic]* of each pulled silicon wafer was measured according to the present invention.

Figure 5:
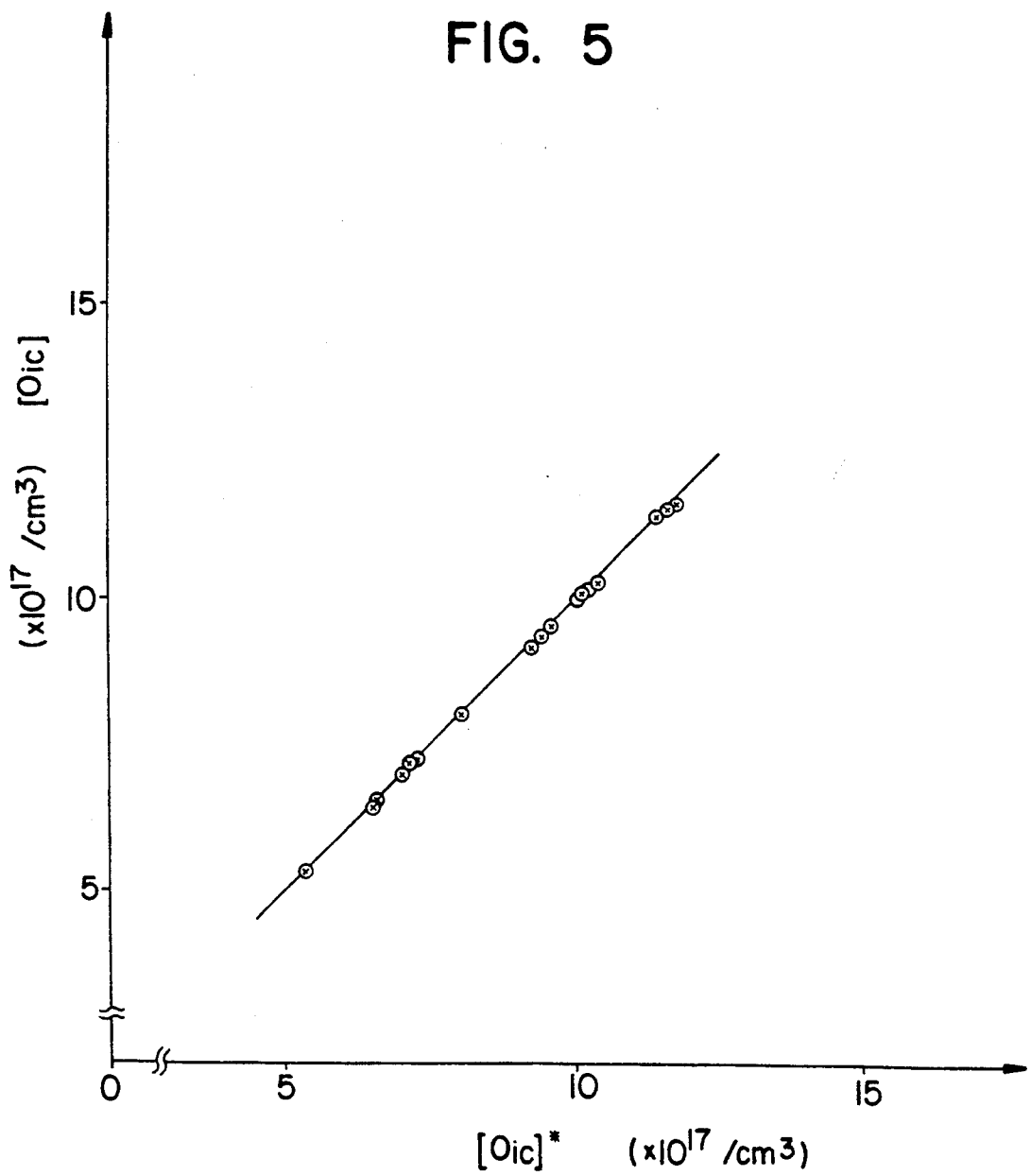
FIGS. 5 to 7 are graphs showing results of other embodiments of the invention.

Such measured results of the interstitial oxygen concentration [Oic] of the one-face mirror polished pulled silicon wafers and the interstitial oxygen concentration [Oic]* of the two-face mirror polished pulled silicon wafers are plotted along the Y-axis and X-axis, respectively, in FIG. 5. As may be seen, the former reasonably corresponds to the latter so that the test results are positioned along the line X=Y.

It is apparent from the examples 23 to 40 that, according to the present invention, the one-face polished pulled silicon wafers and the mirror polished floating zone silicon wafers can be used as specimen and references, respectively, in order to directly measure interstitial oxygen concentration [Oic] of the pulled silicon wafers on the production line.

TABLE 2

| Example No. | interstitial oxygen concentration [Oic] of one-face mirror polished pulled silicon wafer ($\times 10^{17}$ number/cm$^3$) | interstitial oxygen concentration [Oic]* of two-face mirror polished pulled silicon wafer ($\times 10^{17}$ number/cm$^3$) |
|---|---|---|
| 23 | 11.57 | 11.67 |
| 24 | 11.64 | 11.82 |
| 25 | 9.21 | 9.27 |
| 26 | 9.36 | 9.42 |
| 27 | 11.45 | 11.48 |
| 28 | 5.33 | 5.39 |
| 29 | 6.42 | 6.54 |
| 30 | 6.51 | 6.58 |
| 31 | 10.12 | 10.12 |
| 32 | 10.12 | 10.12 |
| 33 | 10.15 | 10.18 |
| 34 | 9.51 | 9.57 |
| 35 | 7.24 | 7.21 |
| 36 | 7.21 | 7.18 |
| 37 | 8.03 | 8.03 |
| 38 | 7.09 | 7.06 |
| 39 | 10.12 | 10.09 |
| 40 | 10.27 | 10.33 |

Embodiment 5A

Another embodiment 5A of the present invention will be explained with respect to the construction and operation thereof.

Embodiment 5A of the present invention has substantially the same construction as that of the above-stated embodiment 5 except that, in addition to the interstitial oxygen concentration measuring step prior to the gettering step, the interstitial oxygen concentration measuring step is carried out after the gettering step.

The interstitial oxygen concentration measuring step after the gettering step has the same construction as that of the interstitial oxygen concentration measuring step prior to the gettering step which corresponds to the measuring step in the above-stated embodiment 5.

The operation of embodiment 5A can be easily understood by taking into consideration that of the above-stated embodiment 5. Thus, the explanation thereof is omitted.

Embodiment 5B

A further embodiment 5B of the present invention will be explained with respect to the construction and operation thereof.

Embodiment 5B of the present invention has substantially the same construction as that of the above-stated embodiment 5 except that, in place of the interstitial oxygen concentration measuring step prior to the gettering step, the interstitial oxygen concentration measuring step is carried out after the gettering step.

The interstitial oxygen concentration measuring step after the gettering step has the same construction as that of the measuring step in the above-stated embodiment 5.

The operation of embodiment 5B can be easily understood by taking into consideration that of the above-stated embodiment 5. Thus, the explanation thereof is omitted.

Embodiment 6

A sixth embodiment of the present invention will be explained with respect to the construction and operation thereof.

The sixth embodiment of the present invention has substantially the same construction as that of the fifth embodiment except that the fourth comparing step and the fifth removing step are omitted.

Embodiment 7

A seventh embodiment of the present invention has the same construction as that of the first embodiment of the present invention except that both front and rear faces of a specimen are mechanically polished, i.e., lapped. After the oxygen concentration [Oic] is measured, the specimens are chemically and mirror polished and the oxygen concentration [Oic]* is again measured.

A method for making a silicon wafer includes the step of measuring the interstitial oxygen concentration after the washing step which follows the mechanically polishing step for silicon wafers on a production line and prior to the chemically polishing step. The measuring step includes a first step of measuring a light transmission characteristic (herein called transmitted light intensity $I_{OBS}$) of a pulled silicon wafer by using parallel polarized light at the Brewster angle B directed onto the pulled silicon wafer. Both the front and rear faces of the wafer are mechanically polished during a mechanical polishing step within the production line and then washed during a washing step. A second step includes measuring a light transmission characteristic (herein called transmitted light intensity $I_O$) of a floating zone silicon wafer functioning as a reference silicon wafer by using parallel polarized light at the Brewster angle B directed onto the reference silicon wafer or floating zone silicon wafer. Both the front and rear faces of the wafer are mirror polished. A third step includes calculating an interstitial oxygen concentration [Oic] on the basis of the light transmission characteristic or transmitted light intensity $I_{OBS}$ of the mechanically polished pulled silicon wafer measured during the first step and the light transmission characteristic or transmitted light intensity $I_O$ of the mirror polished floating zone silicon wafer or reference silicon wafer measured during the second step. A fourth step includes comparing the interstitial oxygen concentration [Oic] of the pulled silicon wafer measured during the third step with a reference value, and a fifth step includes removing a pulled silicon wafer if its interstitial oxygen concentration [Oic] is out of the reference value so as to be defective in view of the comparison results in the fourth step.

In order to obtain a desired flatness, the mechanical polishing step is carried out prior to the chemical polishing step. Damaged or broken layers formed on each surface of the silicon wafer during the step of cutting the silicon single crystal wafer are deleted by chemical polishing.

EXAMPLES 41 TO 46

Working examples of the seventh embodiment will be explained so that a method for making a silicon wafer according to the present invention will be fully understood.

As shown in Table 3, interstitial oxygen concentration [Oic] of plural pulled silicon wafers were measured according to the present invention. First, after both front and rear faces of the silicon wafers were mechanically polished, interstitial oxygen concentration [Oic] thereof was measured.

After that, those pulled silicon wafers were chemically polished and then mirror polished. In such a mirror polished condition, the interstitial oxygen concentration [Oic]* of each pulled silicon wafer was measured according to the present invention.

Figure 6:
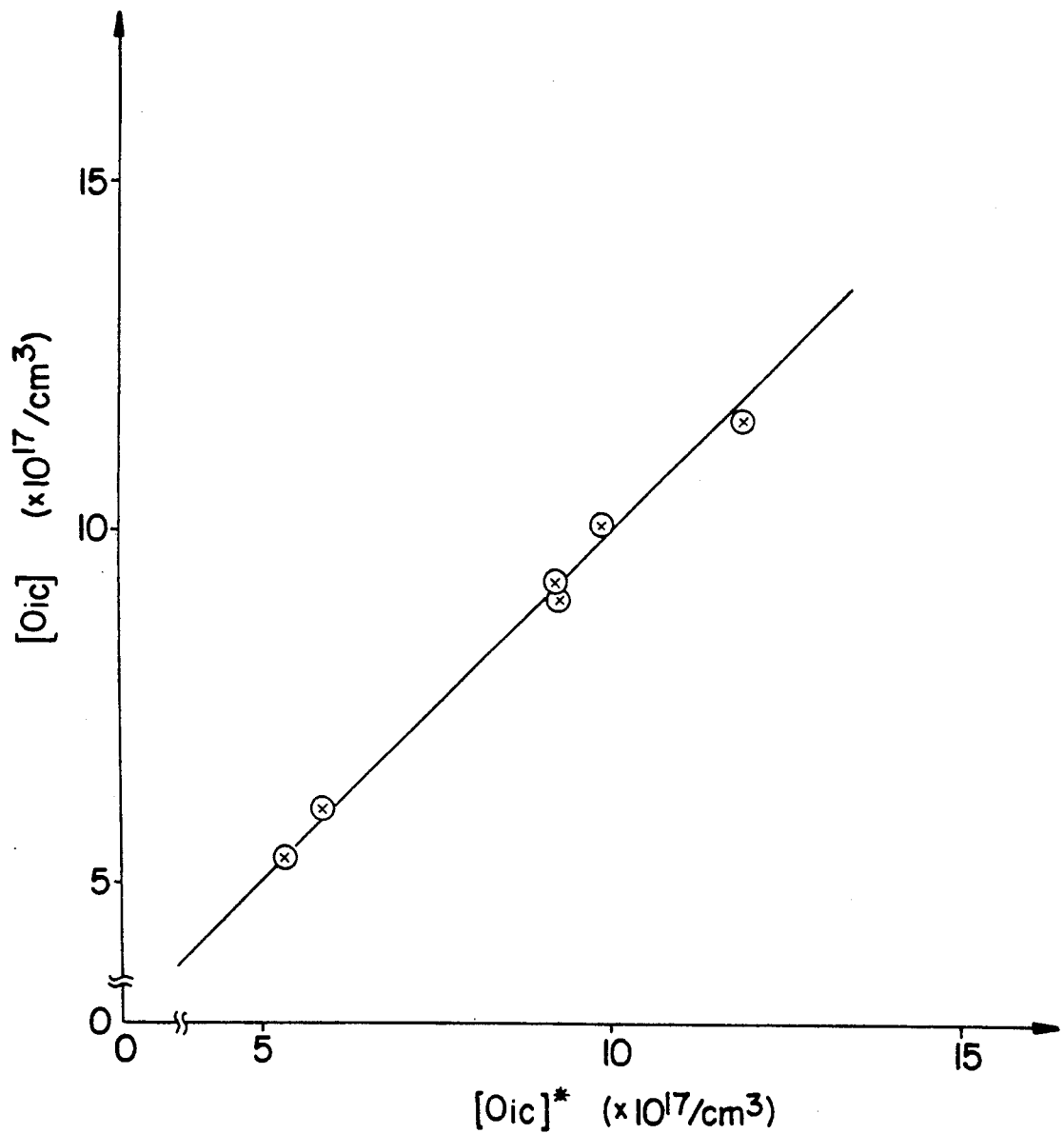

Such measured results of the interstitial oxygen concentration [Oic] of the mechanically polished pulled silicon wafers and the interstitial oxygen concentration [Oic]* of the mirror polished pulled silicon wafers are plotted along the Y-axis and X-axis, respectively, in FIG. 6. This graph shows that the former reasonably corresponds to the latter so that the test results are positioned along the line X=Y.

It is apparent from the examples 41 to 46 that, according to the present invention, the mechanically polished pulled silicon wafers and the mirror polished floating zone silicon wafers can be used as specimen and references, respectively, in order to directly measure interstitial oxygen concentration [Oic] of the pulled silicon wafers on the production line.

TABLE 3

| Example No. | interstitial oxygen concentration [Oic] of mechanically polished pulled silicon wafer ($\times 10^{17}$ number/cm$^3$) | interstitial oxygen concentration [Oic]* of mirror polished pulled silicon wafer ($\times 10^{17}$ number/cm$^3$) |
| --- | --- | --- |
| 41 | 11.60 | 11.90 |
| 42 | 9.23 | 9.30 |
| 43 | 5.35 | 5.40 |
| 44 | 9.05 | 9.28 |
| 45 | 5.92 | 6.01 |
| 46 | 10.10 | 9.94 |

Embodiment 7A

A further embodiment 7A of the present invention will be explained with respect to the construction and operation thereof.

Embodiment 7A of the present invention has substantially the same construction as that of embodiment 7 except that, in addition to the interstitial oxygen concentration measuring step prior to the gettering step, the interstitial oxygen concentration measuring step is carried out after the gettering step.

The interstitial oxygen concentration measuring step after the gettering step has the same construction as that of the interstitial oxygen concentration measuring step prior to the gettering step which corresponds to the measuring step in embodiment 7.

The operation of embodiment 7A can be easily understood by taking into consideration that of embodiment 7. Thus, the explanation thereof is omitted.

Embodiment 7B

Another embodiment 7B of the present invention will be explained with respect to the construction and operation thereof.

This embodiment 7B of the present invention has substantially the same construction as that of the embodiment 7 except that, in place of the interstitial oxygen concentration measuring step prior to the gettering step, the interstitial oxygen concentration measuring step is carried out after the gettering step.

The interstitial oxygen concentration measuring step after the gettering step has the same construction as that of the measuring step in embodiment 7.

The operation of embodiment 7B can be easily understood by taking into consideration that of the embodiment 7. Thus, the explanation thereof is omitted.

Embodiment 8

An eighth embodiment of the present invention will be explained with respect to the construction and operation thereof.

The eighth embodiment of the present invention has substantially the same construction as that of the seventh embodiment except that the fourth comparing step and the fifth removing step are omitted.

A method for making a silicon wafer includes the step of measuring interstitial oxygen concentration after the washing step which follows the mechanically polishing step for silicon wafers on a production line and prior to the chemically polishing step. The measuring step includes a first step of measuring a light transmission characteristic (herein called transmitted light intensity $I_{OBS}$) of a pulled silicon wafer by using parallel polarized light at the Brewster angle B directed onto the pulled silicon wafer. Both the front and rear faces of the wafer are mechanically polished during a mechanical polishing step within the production line and then washed during a washing step but not chemically polished. A second step includes measuring a light transmission characteristic (herein called transmitted light intensity $I_O$) of a floating zone silicon wafer functioning as a reference silicon wafer by using parallel polarized light at the Brewster angle B directed onto the reference silicon wafer or floating zone silicon wafer. Both the front and rear faces of the wafer are mirror polished. A third step includes calculating an interstitial oxygen concentration [Oic] on the basis of the light transmission characteristic or transmitted light intensity $I_{OBS}$ of the mechanically polished pulled silicon wafer measured during the first step and the light transmission characteristic or transmitted light intensity $I_O$ of the mirror polished floating zone silicon wafer or reference silicon wafer measured during the second step.

During the first and second steps, the parallel polarized light enters into both the non-chemically polished pulled silicon wafer and the mirror polished floating zone silicon wafer at the Brewster angle B because any substantial reflection is avoided when the parallel polarized light moves in and through the non-chemically polished pulled silicon wafer and the mirror polished floating zone silicon wafer whereby multiple reflections can be avoided within the non-chemically polished pulled silicon wafer and the mirror polished floating zone silicon wafer.

During the second step, the floating zone silicon wafer is used as a reference silicon wafer because the interstitial oxygen concentration [Oi$_F$] of the floating zone silicon wafer is much smaller than that of the pulled silicon wafer.

Also, both front and rear surfaces of the floating zone silicon wafer are mirror polished because the incidence light or parallel polarized light is intended to be prevented from being scattered at both front and rear surfaces thereof.

During the third step, the interstitial oxygen concentration of the non-chemically polished pulled silicon wafer is calculated on the basis of the light transmission characteristic or transmitted light intensity $I_{OBS}$ of the non-chemically polished pulled silicon wafer measured during the first step and the light transmission characteristic or transmitted light intensity $I_O$ of the floating zone silicon wafer measured during the second step. This calculation is substantially the same as that of the first embodiment.

EXAMPLES 47 TO 55

Working examples of the eighth embodiment will be explained so that a method for making a silicon wafer according to the present invention will be fully understood.

As shown in Table 4, interstitial oxygen concentration [Oic] of plural pulled silicon wafers were measured according to the present invention. First, after the silicon wafers was cut from a single crystal, after it was mechanically polished, interstitial oxygen concentration [Oic] thereof was measured. After that, the pulled silicon wafers were chemically polished and then mirror polished. In such a mirror polished condition, the interstitial oxygen concentration [Oic]* of each pulled silicon wafer was measured according to the present invention.

Figure 7:
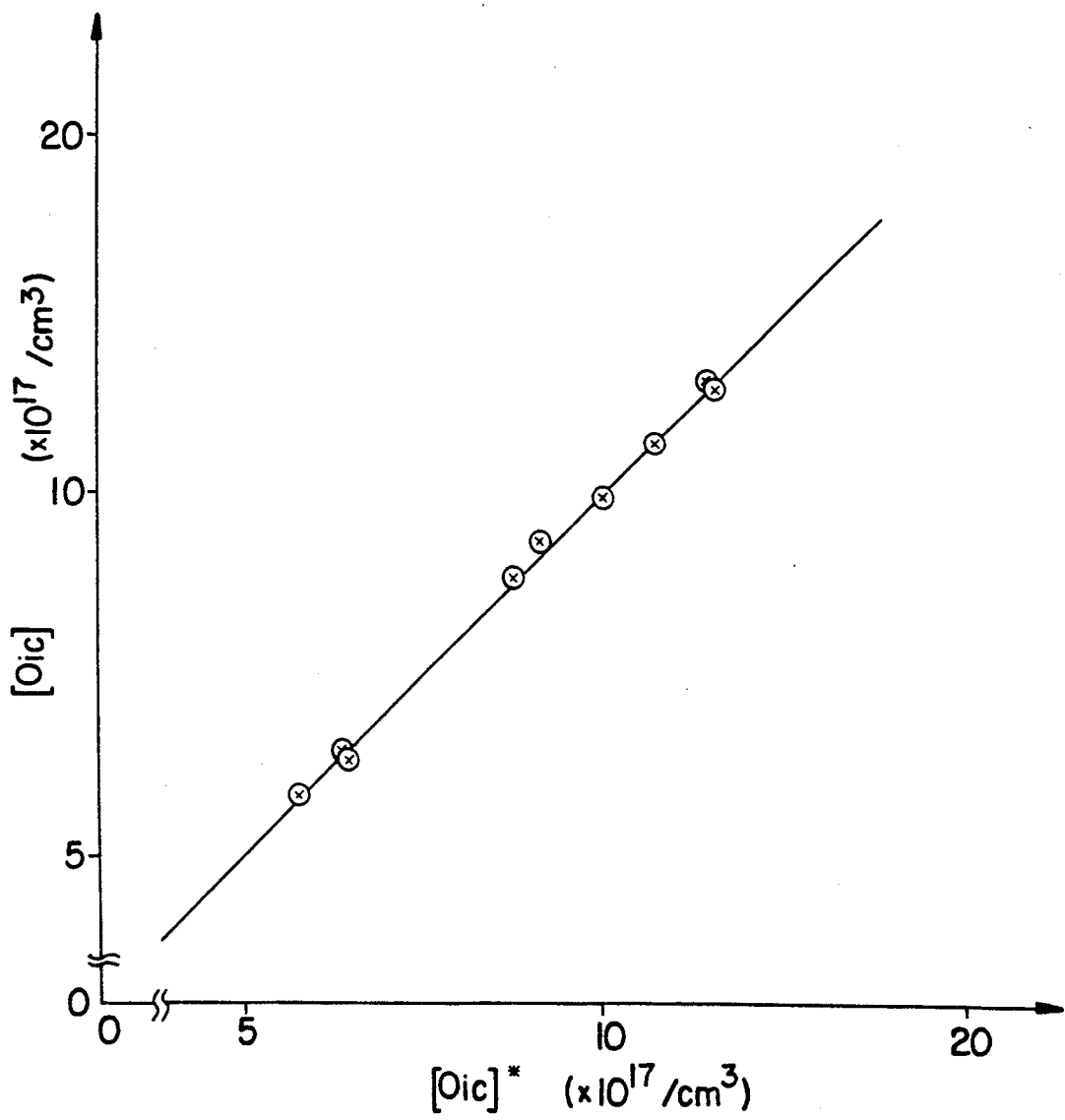

Such measured results of the interstitial oxygen concentration [Oic] of the mechanically polished pulled silicon wafers and the interstitial oxygen concentration [Oic]* of the mirror polished pulled silicon wafers are plotted along the Y-axis and X-axis, respectively, in FIG. 7. This graph shows that the former reasonably corresponds to the latter so that the test results are positioned along the line X=Y.

It is apparent from the examples 47 to 55 that, according to the present invention, the mechanically polished pulled silicon wafers and the mirror polished floating zone silicon wafers can be used as specimen and references, respectively, in order to directly measure interstitial oxygen concentration [Oic] of the pulled silicon wafers on the production line.

TABLE 4

| Example No. | interstitial oxygen concentration [Oic] of mechanically polished pulled silicon wafer ($\times 10^{17}$ number/cm$^3$) | interstitial oxygen concentration [Oic]* of mirror polished pulled silicon wafer ($\times 10^{17}$ number/cm$^3$) |
| --- | --- | --- |
| 47 | 11.60 | 11.50 |
| 48 | 11.50 | 11.60 |
| 49 | 9.32 | 9.16 |
| 50 | 8.89 | 8.77 |
| 51 | 10.70 | 10.80 |
| 52 | 6.45 | 6.37 |
| 53 | 5.85 | 5.79 |
| 54 | 6.35 | 6.44 |
| 55 | 9.96 | 10.10 |

Embodiment 9

Embodiment 9 of the present invention has the same construction as that of embodiment 1 except that the oxygen concentration [Oic] is measured before the mechanical polishing step.

According to embodiment 9 of the present invention, a method for making a silicon wafer includes the steps of cutting a single crystal, washing, gettering (in this case heating) and then mechanically polishing, followed by chemical and mirror polishing. The [Oic] measurement is performed after the washing step and before the gettering and mechanical polishing.

The measuring step in the silicon wafer production method according to the present invention includes a first step of measuring a light transmission characteristic (herein called transmitted light intensity $I_{OBS}$) of a pulled silicon wafer which is cut from a single crystal and then washed but not mechanically polished (herein called non-polished silicon wafer) within the production line, by utilizing parallel polarized light incident at the Brewster angle B into the pulled silicon wafer, a second step of measuring a light transmission characteristic (herein called transmitted light intensity $I_O$) of a floating zone silicon wafer functioning as a reference silicon wafer both front and rear faces of which are mirror polished, by utilizing parallel polarized light incident at the Brewster angle B into the reference silicon wafer or floating zone silicon wafer, a third step of calculating an interstitial oxygen concentration [Oic] on the basis of the light transmission characteristic or transmitted light intensity $I_{OBS}$ of the non-mechanically polished pulled silicon wafer measured during the first step and the light transmission characteristic or transmitted light intensity $I_O$ of the mirror polished floating zone silicon wafer or reference silicon wafer measured during the second step, a fourth step of comparing the interstitial oxygen concentration [Oic] of the pulled silicon wafer measured during the third step with a reference value, and a fifth step of removing a pulled silicon wafer if its interstitial oxygen concentration [Oic] is outside of a range about the reference value so as to be defective in view of the results compared in the fourth step.

EXAMPLES 56 TO 64

Working examples of a ninth embodiment correspond to the working examples of the eighth embodiment, respectively.

Like in Table 4, interstitial oxygen concentration [Oic] of plural pulled silicon wafers were measured according to the present invention. First, after the silicon wafers was cut from a single crystal, before it was mechanically polished, the interstitial oxygen concentration [Oic] thereof was measured. After that, the pulled silicon wafers were mechanically polished, chemically polished and then mirror polished. In such a mirror polished condition, the interstitial oxygen concentration [Oic]* of each pulled silicon wafer was measured according to the present invention.

Such measured results of the interstitial oxygen concentration [Oic] of the non-mechanically polished pulled silicon wafers and the interstitial oxygen concentration [Oic]* of the mirror polished pulled silicon wafers are plotted in FIG. 7.

Embodiment 10

A tenth embodiment of the present invention will be explained with respect to the construction and operation thereof.

The tenth embodiment of the present invention has substantially the same construction as that of the ninth embodiment except that, in addition to the interstitial oxygen concentration measuring step prior to the gettering step, the interstitial oxygen concentration measuring step is carried out prior to the mechanical polishing, subsequent to the gettering step.

The interstitial oxygen concentration measuring step after the gettering step has the same construction as that of the interstitial oxygen concentration measuring step prior to the gettering step which corresponds to the measuring step in the ninth embodiment.

The operation of the tenth embodiment can be easily understood by taking into consideration that of the ninth embodiment. Thus, the explanation thereof is omitted.

Embodiment 11

An eleventh embodiment of the present invention will be explained with respect to the construction and operation thereof.

The eleventh embodiment of the present invention has substantially the same construction as that of the ninth embodiment except that, in place of the interstitial oxygen concentration measuring step prior to the gettering step, the interstitial oxygen concentration measuring step is carried out prior to the mechanical polishing step following the gettering step.

The interstitial oxygen concentration measuring step after the gettering step has the same construction as that of the measuring step in the ninth embodiment.

The operation of the eleventh embodiment can be easily understood by taking into consideration that of the ninth embodiment. Thus, the explanation thereof is omitted.

What is claimed is:

1. A silicon wafer measuring method including:
   (a) a first step of measuring a light transmission characteristic ($I_{OBS}$) of a pulled silicon wafer by utilizing parallel polarized light incident at the Brewster angle into the pulled silicon wafer;
   (b) a second step of measuring a light transmission characteristic ($I_O$) of a floating zone silicon wafer functioning as a reference silicon wafer both front and rear faces of which are mirror polished, by utilizing parallel polarized light incident at the Brewster angle into the floating zone silicon wafer; and
   (c) a third step of directly calculating an interstitial oxygen concentration throughout said pulled silicon wafer on the basis of the light transmission characteristic ($I_{OBS}$) of the pulled silicon wafer measured during the first step and the light transmission characteristic ($I_O$) of the floating zone silicon wafer measuring during the second step.

2. A silicon wafer measuring method as defined in claim 1, further including:
   (d) a fourth step of comparing the interstitial oxygen concentration [Oic] of the pulled silicon wafer measured during the third step with a reference value.

3. A silicon wafer measuring method as defined in claim 2, further including:
   (e) a fifth step of removing the pulled silicon wafer if its interstitial oxygen concentration [Oic] is outside of a range about the reference value and thereby determined to be defective.

4. A silicon wafer production method in which a pulled silicon wafer cut from a pulled silicon single crystal is subject to a series of treatment, said production method including:
   (a) a first step of measuring a light transmission characteristic ($I_{OBS}$) of the pulled silicon wafer by utilizing parallel polarized light incident at the Brewster angle into the pulled silicon wafer;
   (b) a second step of measuring a light transmission characteristic ($I_O$) of a floating zone silicon wafer functioning as a reference silicon wafer both front and rear faces of which are mirror polished, by utilizing parallel polarized light incident at the Brewster angle into the floating zone silicon wafer; and
   (c) a third step of directly calculating an interstitial oxygen concentration [Oic] throughout said pulled silicon wafer on the basis of the light transmission characteristic ($I_{OBS}$) of the pulled silicon wafer measured during the first step and the light transmission characteristic ($I_O$) of the floating zone silicon wafer measured during the second step.

5. A silicon wafer production method as defined in claim 4 in which the series of treatments include mechanical cutting, mechanical polishing, chemically polishing, mirror polishing, detecting defective wafers, removing defective wafers, washing, and gettering.

6. A silicon wafer production method including:
   (a) a first step of measuring a light transmission characteristic or transmitted light intensity ($I_{OBS}$) of a pulled silicon wafer both front and rear faces of which are chemically polished within a production line and then washed, by utilizing parallel polarized light incident at the Brewster angle (B) into the pulled silicon wafer;
   (b) a second step of measuring a light transmission characteristic or transmitted light intensity ($I_O$) of a floating zone silicon wafer functioning as a reference silicon wafer both front and rear faces of which are mirror polished, by utilizing parallel polarized light at Brewster angle (B) into the reference silicon wafer or floating zone silicon wafer; and
   (c) a third step of directly calculating an interstitial oxygen concentration [Oic] throughout said chemically polished pulled silicon wafer on the basis of the light transmission characteristic or transmitted light intensity ($I_{OBS}$) of the chemically polished pulled silicon wafer measured during the first step and the light transmission characteristic or transmitted light intensity ($I_O$) of the mirror polished floating zone silicon water or reference silicon wafer measured during the second step.

7. The silicon wafer production method of claim 6, further including:
   (d) a further step of comparing the interstitial oxygen concentration [Oic] of the pulled silicon wafer measured during the third step with a reference value.

8. The silicon wafer production method of claim 7, further including:
   (e) a fifth step of removing the pulled silicon wafer if its interstitial oxygen concentration [Oic] is outside of a range about the reference value and thereby determined to be defective.

9. A silicon wafer production method including:
   (a) a first step of measuring a light transmission characteristic or transmitted light intensity ($I_{OBS}$) of a pulled one-face polished silicon wafer only a front face of which is mirror polished within a production line and then washed, by utilizing parallel polarized light incident at the Brewster angle (B) into the pulled silicon wafer;

(b) a second step of measuring a light transmission characteristic or transmitted light intensity ($I_O$) of a floating zone silicon wafer functioning as a reference silicon wafer both front and rear faces of which are mirror polished, by utilizing parallel polarized light incident at the Brewster angle (B) into the reference silicon wafer or floating zone silicon wafer; and (c) a third step of directly calculating an interstitial oxygen concentration [Oic] throughout said one-face polished pulled silicon wafer on the basis of the light transmission characteristic or transmitted light intensity ($I_{OBS}$) of the one-face polished pulled silicon wafer measured during the first step and the light transmission characteristic or transmitted light intensity ($I_O$) of the mirror polished floating zone silicon wafer or reference silicon wafer measuring during the second step.

10. The silicon wafer production method of claim 9, further including:

(d) a fourth step of comparing the interstitial oxygen concentration [Oic] of the pulled silicon wafer measured during the third step with a reference value.

11. The silicon wafer production method of claim 10, further including:

(e) a fifth step of removing the pulled silicon wafer if its interstitial oxygen concentration [Oic] is outside of a range about the reference value and thereby determined to be defective.

12. The silicon wafer production method of claim 11, in which the fourth step consists of comparing the interstitial oxygen concentration [Oic] to an upper and lower reference value.

13. A silicon wafer production method including:

(a) a first step of measuring a light transmission characteristic or transmitted light intensity ($I_{OBS}$) of a pulled silicon wafer both front and rear faces of which are mechanically polished within a production line and then washed, by utilizing parallel polarized light incident at the Brewster angle (B) into the pulled silicon wafer;

(b) a second step of measuring a light transmission characteristic or transmitted light intensity ($I_O$) of a floating zone silicon wafer functioning as a reference silicon wafer both front and rear faces of which are mirror polished, by utilizing parallel polarized light incident at the Brewster angle (B) into the reference silicon wafer or floating zone silicon wafer; and (c) a third step of directly calculating an interstitial oxygen concentration [Oic] throughout said mechanically polished pulled silicon wafer on the basis of the light transmission characteristic or transmitted light intensity ($I_{OBS}$) of the mechanically polished pulled silicon wafer measured during the first step and the light transmission characteristic or transmitted light intensity ($I_O$) of the mirror polished floating zone silicon wafer or reference silicon wafer measured during the second step.

14. A silicon wafer production method as defined in claim 13, further including:

(d) a fourth step of comparing the interstitial oxygen concentration [Oic] of the pulled silicon wafer measured during the third step with a reference value.

15. A silicon wafer production method as defined in claim 14, further including:

(e) a fifth step of removing the pulled silicon wafer if its interstitial oxygen concentration [Oic] is outside of a range about the reference value and thereby determined to be defective.

16. A silicon wafer production method including:

(a) a first step of measuring a light transmission characteristic or transmitted light intensity ($I_{OBS}$) of non-polished pulled silicon wafer which is cut from a single crystal and then washed but not mechanically polished within a production line, by utilizing parallel polarized light incident at the Brewster angle (B) into the pulled silicon wafer;

(b) a second step of measuring a light transmission characteristic or transmitted light intensity ($I_O$) of a floating zone silicon wafer functioning as a reference silicon wafer both front and rear faces of which are mirror polished, by utilizing parallel polarized light incident at the Brewster angle (B) into the reference silicon wafer or floating zone silicon wafer; and (c) a third step of directly calculating an interstitial oxygen concentration [Oic] throughout said non-polished pulled silicon wafer on the basis of the light transmission characteristic or transmitted light intensity ($I_{OBS}$) of the non-polished pulled silicon wafer measured during the first step and the light transmission characteristic or transmitted light intensity ($I_O$) of the mirror polished floating zone silicon wafer or reference silicon wafer measuring during the second step.

17. A silicon wafer production method as defined in claim 16, further including:

(d) a fourth step of comparing the interstitial oxygen concentration [Oic] of the pulled silicon wafer measured during the third step with a reference value.

18. A silicon wafer production method as defined in claim 17, further including:

(e) a fifth step of removing the pulled silicon wafer if its interstitial oxygen concentration [Oic] is outside of a range about the reference value and thereby determined to be defective.

19. A silicon wafer production method including:

(a) a first step of measuring a light transmission characteristic or transmitted light intensity ($I_{OBS}$) of a pulled silicon wafer both front and rear faces of which are mechanically polished within a production line and then washed but not chemically polished, by utilizing parallel polarized light incident at the Brewster angle (B) into the pulled silicon wafer;

(b) a second step of measuring a light transmission characteristic or transmitted light intensity ($I_O$) of a floating zone silicon wafer functioning as a reference silicon wafer both front and rear faces of which are mirror polished, by utilizing parallel polarized light incident at Brewster angle (B) into the reference silicon wafer or floating zone silicon wafer; and (c) a third step of directly calculating an interstitial oxygen concentration [Oic] throughout said mechanically polished pulled silicon wafer on the basis of the light transmission characteristic or transmitted light intensity ($I_{OBS}$) of the mechanically polished pulled silicon wafer measured during the first step and the light transmission characteristic or transmitted light intensity ($I_O$) of the mirror polished floating zone silicon wafer or reference silicon wafer measured during the second step.

20. A silicon wafer production method as defined in claim 19, further including:
(d) a fourth step of comparing the interstitial oxygen concentration [Oic] of the pulled silicon wafer measured during the third step with a reference value.

21. A silicon wafer production method as defined in claim 20, further including:
(e) a fifth step of removing the pulled silicon wafer if its interstitial oxygen concentration [Oic] is outside of a range about the reference value and thereby determined to be defective.

22. A method for measuring an interstitial oxygen concentration, said method comprising the steps of:
(1) providing a pulled silicon wafer, said pulled silicon wafer having an interstitial oxygen concentration to be measured and having a front face and a rear face, said front face having one of a plurality of predetermined finishes and said rear face having one of said plurality of predetermined finishes,
(2) providing a floating zone silicon wafer, said floating zone silicon wafer functioning as a reference silicon wafer and having both front and rear faces which are mirror polished;
(3) measuring a first light transmission characteristic of said pulled silicon wafer by utilizing parallel polarized light incident at the Brewster angle into said pulled silicon wafer;
(4) measuring a second light transmission characteristic of said floating zone silicon wafer by utilizing parallel polarized light incident at the Brewster angle into said floating zone silicon wafer; and
(5) calculating said interstitial oxygen concentration throughout said pulled silicon wafer on the basis of said first light transmission characteristic and said second light transmission characteristic.

23. A method as recited in claim 22 wherein said plurality of predetermined finishes include a mechanically polished finish, a chemically polished finish and a mirror polished finish.

* * * * *

Disclaimer

5,287,167 — Shirai et al., Kanagawa (JP). METHOD FOR MEASURING INTERSTITIAL OXYGEN CONCENTRATION. Patent dated February 15, 1994, Disclaimer filed February 22, 2005, by the Assignee, Toshiba Ceramics Co., Ltd.

This patent is subject to a terminal disclaimer.

*(Official Gazette June 14, 2005)*